United States Patent [19]

De Vries et al.

[11] Patent Number: 4,489,068
[45] Date of Patent: Dec. 18, 1984

[54] METHOD AND COMPOSITION FOR ENHANCING THE INSECTICIDAL ACTIVITY OF CERTAIN ORGANOPHOSPHORUS COMPOUNDS

[75] Inventors: Donald H. De Vries, Concord; Walter Reifschneider, Walnut Creek; Mark J. Costales, Concord, all of Calif.

[73] Assignee: The Dow Chemical Company, Midland, Mich.

[21] Appl. No.: 489,421

[22] Filed: Apr. 28, 1983

[51] Int. Cl.³ ............... A01N 57/16; A01N 57/32; C07F 9/65

[52] U.S. Cl. ..................... 424/200; 544/123; 544/243

[58] Field of Search ............ 424/200; 544/243, 123

[56] References Cited

U.S. PATENT DOCUMENTS

| | | | |
|---|---|---|---|
| 3,159,630 | 12/1964 | Rigterink | 544/243 |
| 3,244,586 | 4/1966 | Rigterink | 424/200 |
| 3,663,544 | 5/1972 | Milzner et al. | 544/243 |
| 3,808,333 | 4/1974 | Milzner et al. | 544/243 |
| 3,928,353 | 12/1975 | Milzner et al. | 544/243 |
| 3,966,730 | 6/1976 | Hofer et al. | 544/243 |
| 4,045,561 | 8/1977 | Mühle et al. | 544/123 X |
| 4,159,323 | 6/1979 | Maurer et al. | 424/200 |
| 4,202,889 | 5/1980 | Maurer et al. | 424/200 |
| 4,213,975 | 7/1980 | Larson | 424/200 |
| 4,223,026 | 9/1980 | Larson | 424/200 |
| 4,261,983 | 4/1981 | Maurer et al. | 424/200 |
| 4,353,897 | 10/1982 | Bock et al. | 424/200 |
| 4,380,538 | 4/1983 | Maurer et al. | 424/200 |

Primary Examiner—Donald G. Daus
Assistant Examiner—Diana G. Rivers
Attorney, Agent, or Firm—S. Preston Jones; Ronald G. Brookens

[57] ABSTRACT

The insecticidal activity of certain pyridinyl phosphorus compounds is enhanced by the admixture therewith of certain 2,5,6-trisubstituted-4-pyrimidinyl phosphoramidates or phosphoramidothioates.

32 Claims, No Drawings

METHOD AND COMPOSITION FOR ENHANCING THE INSECTICIDAL ACTIVITY OF CERTAIN ORGANOPHOSPHORUS COMPOUNDS

BACKGROUND OF THE INVENTION

Organophosphorus compounds are as a group one of the most widely-used insecticides in agriculture. The pyridinyl phosphorus insecticides are a highly active group of compounds used for the kill and control of a great variety of insects.

It has been found, however, that certain pyridinyl phosphorus insecticides are not highly effective in the kill and control of insects of the order Lepidoptera and especially of the genus Heliothis. The reasons for the ineffectiveness of these pyridyl phosphorus insecticides are not fully known nor understood. It is believed that by some mechanism, insects from the above group are insensitive to these phosphorus compounds. Since these insects are of economic importance, methods are continually being sought to increase the activity of these insecticides in the control of insects of the order Lepidoptera.

SUMMARY OF THE INVENTION

The present invention is directed to a method of and compositions for enhancing the insecticidal activity of certain pyridinyl phosphorus insecticides which comprises admixing with the pyridinyl phosphorus insecticide, an activity enhancing amount of a 2,5,6-trisubstituted-4-pyrimidinyl phosphoramidate or phosphoramidothioate.

As indicated hereinabove, certain pyridinyl phosphorus insecticides have been found to be ineffective in the kill and control of insects of the order Lepidoptera and especially of the genus Heliothis. This ineffectiveness is not fully known or understood. It has been suggested that by some mechanism, insects from the above group have the ability to detoxify or otherwise inhibit the insecticidal activity of the phosphorus compounds.

In order to overcome or bypass this ineffectiveness, prior methods have involved the use of larger treating or dosage amounts of the insecticide or the use of an additional insecticide which is active against insects of the order Lepidoptera. Neither the use of larger dosages nor the use of an additional insecticide has proven to be satisfactory.

The present invention is conducted by contacting insects of the order Lepidoptera and especially the genus Heliothis or their habitat with a composition containing one part of the insecticidally active pyridinyl phosphorus compound to be enhanced and from about 1/16 part to about 16 parts of the 2,5,6-trisubstituted-5-pyrimidinyl phosphoramidate or phosphoramidothioate, i.e., a ratio of about 16:1 to about 1:16. A preferred ratio is from about 8:1 to about 1:1 with the most preferred ratio being from about 8:1 to about 2:1.

The exact mechanism by which the pyrimidinyl phosphoramidates or phosphoramidothioates are able to enhance the activity of the pyridinyl phosphorus compounds is not fully understood. One theory, for which the applicants do not wish to be bound, suggests that insects of the order Lepidoptera and especially of the genus Heliothis possess an acetylcholinesterase enzyme which is partially insensitive to the pyridinyl phosphorus compounds. The pyrimidinyl phosphoramidothioates are thought to modify the acetylcholinesterase enzyme such that its sensitivity to pyridinyl phosphorus compounds is increased.

The pyrimidinyl phosphoramidothioates are themselves poor insecticides but when employed with the pyridinyl phosphorus compounds, appear to make insects of the order Lepidoptera susceptible to the insecticidal action of the pyridinyl phosphorus compounds.

The pyridinyl phosphorus insecticides found to be enhanced by the pyrimidinyl phosphoramidates or phosphoramidothioates are those which correspond to the formula

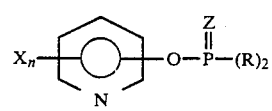

(Formula I)

wherein each X independently represents bromo, chloro, fluoro or iodo; Z represents oxygen or sulfur; each R independently represents alkoxy of 1 to 4 carbon atoms and n represents an integer of from 1 to 3.

The preferred pyridinyl phosphorus insecticides are those compounds wherein X is chloro or fluoro and Z is sulfur. The most preferred insecticides are those compounds wherein X is chloro, n is 3, Z is sulfur and R is methoxy or ethoxy. These compounds, their methods of preparation and their insecticidal uses are taught in U.S. Pat. No. 3,244,586.

The pyrimidinyl phosphoramidates or phosphoramidothioates which are employed as activity enhancers are derivatives of 4-pyrimidinols and correspond to the formula

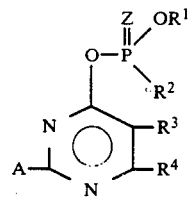

(Formula II)

wherein A represents hydrogen, alkyl of 1 to 4 carbon atoms, alkylthio of 1 to 4 carbon atoms, allylthio, cycloalkyl of 3 or 4 carbon atoms, alkyl(cycloalkyl) wherein the alkyl group is of 1 to 4 carbon atoms and the cycloalkyl group is of 3 or 4 carbon atoms, (cycloalkyl)alkyl wherein the alkyl group is of 1 to 4 carbon atoms and the cycloalkyl group is of 3 or 4 carbon atoms, phenyl, trifluoromethyl, dialkylamino wherein each alkyl group is independently of 1 to 4 carbon atoms or morpholino; $R^1$ represents alkyl of 1 to 4 carbon atoms; $R^2$ represents monoalkylamino of 1 to 4 carbon atoms, dialkylamino wherein each alkyl group is independently of 1 to 4 carbon atoms, allylamino, ((dimethylamino)methylene)amino ($-N=CH-N(CH_3)_2$) or monocycloalkylamino of 3 to 4 carbon atoms; $R^3$ represents hydrogen, chloro, bromo, fluoro or methyl; $R^4$ represents hydrogen, chloro, trifluoromethyl, alkyl of 1 to 4 carbon atoms, alkylthio of 1 to 4 carbon atoms; (alkylthio)alkyl wherein each alkyl group is independently of 1 to 4 carbon atoms, alkoxyalkyl wherein the alkoxy and alkyl groups are independently of 1 to 4 carbon atoms, cycloalkyl of 3 or 4 carbon atoms or a group of the formula

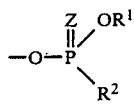

and Z is oxygen or sulfur.

The preferred pyrimidinyl compounds are those wherein A represents hydrogen, alkyl, cycloalkyl, or alkylthio; Z is sulfur; $R^1$ represents alkyl of 1 to 3 carbon atoms; $R^2$ represents monoalkylamino, ((dimethylamino)methylene)amino or cycloalkylamino; $R^3$ represents hydrogen or chloro and $R^4$ represents hydrogen, alkyl, cyclopropyl or chloro.

A most preferred group of the pyrimidinyl compounds include those compounds wherein A represents alkyl, cycloalkyl or ethylthio; Z is sulfur; $R^1$ is ethyl; $R^2$ represents monoalkylamino or cyclopropylamino; $R^3$ represents hydrogen or chloro and $R^4$ represents methyl, cyclopropyl or chloro.

In the present specification and claims, the terms "alkyl", "alkoxy", "alkylthio", "dialkylamino" and "monoalkylamino" are employed to designate alkyl, alkoxy, alkylthio, monoalkylamino and dialkylamino radicals wherein the alkyl portion can be either straight or branched chained.

The pyrimidinyl compounds are for the most part known and are taught in U.S. Pat. Nos. 2,754,243; 3,159,630; 3,951,975; 3,966,730; 4,012,506; 4,202,889; 4,254,113 and 4,261,983, European patent No. G007-466 (Derwent, Agdock, Week D-17, C-1), German patent No. 2,951,350 (Derwent, Agdoc, Week D-28, C-1), Japanese patent No. 23181 (CA. 60:P5520e), German Offen. 2,831,852 (CA. 93:114559q) and German Offen. 2,830,766 (CA. 93:114700d). The pyrimidinyl compound employed herein can be prepared as taught in these references or by methods analogous to the methods taught therein.

Those pyrimidinyl compounds which correspond to one of the formulae

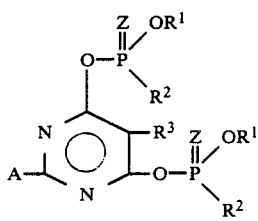

(Formula III)

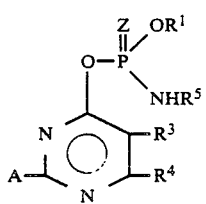

(Formula IV)

wherein A, Z, $R^1$, $R^2$, $R^3$ and $R^4$ are as hereinabove defined and $R^5$ is cycloalkyl of 3 or 4 carbon atoms are also novel compounds and constitute a part of the present invention. While these compounds and their preparation are not taught by the above set-forth references, they can for the most part be prepared employing procedures analogous to those taught in said references employing the appropriate starting materials.

In a representative procedure for preparing most of the pyrimidinyl compounds, substantially equimolar amounts of an appropriate pyrimidinol reactant corresponding to the formula

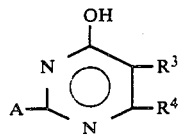

(Formula V)

and an appropriate chlorophosphorus reactant corresponding to the formula

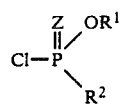

(Formula VI)

are reacted together in the presence of a solvent and a HCl absorber at a temperature in the range of from about 10° C. to about 100° C. This preparative procedure can be represented by the following reaction scheme

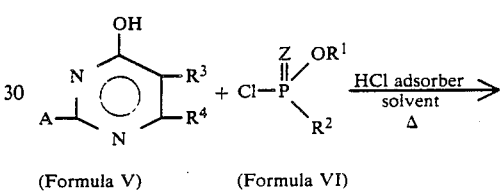

(Formula V)    (Formula VI)

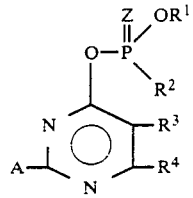

(Formula II)

wherein A, Z, $R^1$ and $R^2$ are as hereinbefore defined. No attempt has been made to present a balanced equation.

Those compounds wherein $R^4$ is

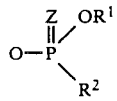

(Formula VII)

can be prepared by employing 2 moles of the appropriate chlorophosphorus reactant per mole of the appropriate 4,6-pyrimidinediol.

Representative solvents include those taught in the above references such as, for example, acetonitrile, cyclohexane, benzene, toluene, xylene, acetone, methylene chloride, methylethylketone, diethylether, dioxane, tetrahydrofuran and the like, with a preferred solvent being acetonitrile. Representative HCl absorbers include those taught in the above references such as, for example, alkali metal carbonates such as sodium or potassium carbonate, alkali metal hydroxides such as sodium or potassium hydroxide and tertiary amines such as, for example, trimethylamine, triethylamine, pyridine and the like, with a preferred absorber being potassium carbonate.

After the completion of the reaction, the insoluble salts are removed by filtration and the filtrate concentrated by evaporation under reduced pressure. The product which remains as a residue is purified by taking up the residue in a solvent such as ether and washing the mixture with a dilute alkaline material such as dilute sodium hydroxide and then with a saturated brine solution such as saturated sodium chloride. The mixture is dried and the solvent removed leaving the desired product.

The compounds of the present invention which correspond to the formula

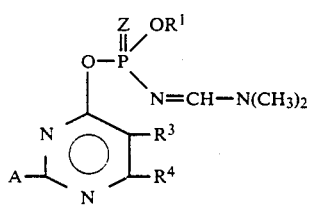

(Formula VIII)

wherein A, Z, $R^1$, $R^3$ and $R^4$ are as hereinbefore defined, can be prepared by the reaction of a molar equivalent of an appropriate 4-pyrimidinyl phosphoramidothioate or phosphoramidate corresponding to the formula

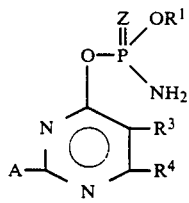

(Formula IX)

with from about a 10 to about a 30 percent excess of dimethylformamide dimethyl acetal.

In carrying out this reaction, the dialkylacetal reactant is added to a solution of the phosphoramidothioate (phosphoramidate) reactant in a solvent such as methylene chloride, diethylether, toluene, or carbon tetrachloride. The mixture is stirred at room temperature for from about 30 minutes to about 4 hours. The solvent is then removed by evaporation. The crude product which remains as a residue is taken up in a solvent such as ether (ethyl ether) and the ether solution washed with water and then a saturated sodium chloride solution. The ether solution is then dried and the ether is removed by evaporation leaving the desired product.

The 4-pyrimidinyl phosphoramidothioate or phosphoramidate employed as a starting material and corresponding to the formula

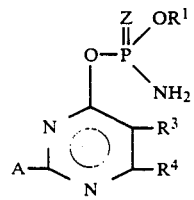

(Formula X)

wherein A, Z, $R^1$, $R^3$ and $R^4$ are as hereinabove defined can be prepared by bubbling excess ammonia into a stirring mixture of a 4-pyrimidinyl phosphorochloridothioate or phosphorochloridate reactant in a solvent such as acetonitrile. The reaction is usually carried out at a temperature of from about minus (−) 10° to about 80° C. for a period of from about one to about 16 or more hours. After the completion of the reaction, the reaction mixture is filtered and the residue remaining is purified by high pressure liquid chromatography, if necessary.

The 4-pyrimidinyl phosphorochloridothioate or phosphorochloridate employed as a starting material in the above reaction can be prepared by reacting substantially equimolar amounts of an appropriate 4-pyrimidinol reactant corresponding to the formula

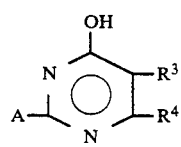

(Formula XI)

wherein A, $R^3$ and $R^4$ are as hereinbefore defined, and an appropriate phosphorodichloridate or phosphorodichloridothioate corresponding to the formula

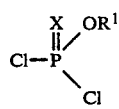

(Formula XII)

wherein $R^1$ is as hereinbefore defined in the presence of a solvent and a hydrogen chloride absorber.

In carrying out the reaction, the reactants are mixed in any suitable fashion and maintained together with agitation until the reaction is complete. It is convenient to first mix the pyrimidinol with the solvent and the phosphorus reactant and then add the HCl acceptor. The reaction is complete when all of the phosphorus reactant has been consumed.

Representative solvents include, for example, acetonitrile, cyclohexane, benzene, toluene, xylene, acetone, methylene chloride, methylethylketone, diethylether, dioxane, tetrahydrofuran and the like.

Representative hydrogen chloride absorbers (acid-binding agents) include, for example, alkali metal carbonates such as sodium and potassium carbonates and tertiary amines such as, for example, trimethylamine, triethylamine, pyridine and the like.

At the completion of the reaction, the reaction mixture is filtered to remove any insolubles and the filtrate is concentrated under reduced pressure. The residue is then taken up in ethyl ether, benzene, toluene, methylene chloride or chloroform and washed thoroughly with water and then with a saturated sodium chloride solution and dried. The solvent is removed by evaporation under reduced pressure leaving the desired product.

While the above discussion is directed to the preparation and separation and recovery of each of the intermediates prior to its use in the next step, the present compounds can also be prepared in situ with no separation of the intermediates.

PREPARATION OF STARTING MATERIALS

The N-cyclopropy O-alkyl phosphoramidochloro compounds corresponding to the formula

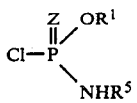                                (Formula XIII)

wherein Z, $R^1$ and $R^5$ are as hereinbefore defined, can be prepared by reacting an alkyl phosphorodichloridothioate or alkyl phosphorodichloridate with a substantially two molar amount of cyclopropylamine in the presence of an inert solvent.

In carrying out this reaction cyclopropylamine is added slowly to a stirred solution of an alkyl phosphorodichloridothioate or an alkyl phosphorodichloridate. The reaction is carried out at a temperature of approximately 0° C. The reaction is complete when all of the phosphorus reactant has been consumed.

Representative solvents include, for example, methylene chloride, ether, benzene, toluene and the like.

At the completion of the reaction, the reaction mixture is filtered to remove precipitated cyclopropylamine hydrochloride and the filtrate concentrated under reduced pressure. The residue can be used directly or be purified by distillation under vacuum.

The 4-pyrimidinols employed as starting materials can, for the most part, be prepared by the reaction of substantially equimolar amounts of an appropriate amidine, in the form of an acid salt, with an appropriate acylacetic acid ester. The reaction is carried out in the presence of an alkanol such as methanol or ethanol and an alkali metal alkoxide solution such as sodium or potassium methoxide or ethoxide under reflux conditions for about 2–4 hours. This preparative procedure can be represented by the following reaction scheme

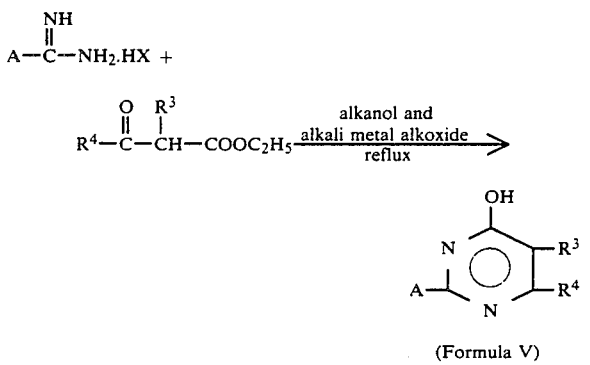

(Formula V)

wherein A, $R^3$, $R^4$ and X are as hereinbefore defined.

After the reaction is complete, the reaction mixture is concentrated under vacuum. Water is added to the residue and the resulting mixture brought to a pH of between 5 and 7 by the addition of an acid such as hydrochloric acid or acetic acid. The product which precipitates out is recovered by filtration, washed with water and dried. The product can be purified by recrystallization from a solvent such as ethanol or cyclohexane. The product can be employed as such without the final purification step.

The 4,6-pyrimidinediols employed as intermediates can be prepared by the reaction of an appropriate amidine with an appropriate diethyl malonate. This preparative procedure can be represented by the following reaction scheme

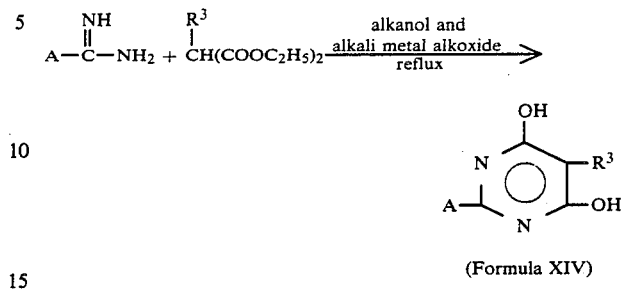

(Formula XIV)

The reaction and recovery procedure is the same as set forth hereinabove.

The 6-cycloalkyl-4-pyrimidinols employed as intermediates in the preparation of the present compounds are for the most part known compounds, and can be prepared according to methods described in the literature or by methods analogous to said methods. A review of various methods for the preparation of 4-pyrimidinols can be found in the volumes "The Pyrimidines" (1962, 1970) of the monograph series "The Chemistry of Heterocyclic Compounds" (Editor: A. Weissberger; Publisher: Interscience Publishers, a division of John Wiley and Sons).

Some compounds, for example, 6-cyclopropyl-2-methyl-4-pyrimidinol, 6-cyclopropyl-2-methylthio-4-pyrimidinol, 6-cyclopropyl-2-methoxy-4-pyrimidinol and 6-cyclopropyl-2-methoxy-5-methyl-4-pyrimidinol can also be prepared according to the method of M. Zimmermann, U.S. Pat. No. 3,457,278 (1969) in which acetamidine hydrochloride, S-methylisothiourea sulfate or O-methylisourea hydrochloride, respectively, is reacted with β-oxocyclopropanepropionate or with α-methyl-β-oxocyclopropanepropionate.

6-Cyclopropyl-4-pyrimidinol can also be prepared by desulfurization of 6-cyclopropyl-2-mercapto-4-pyrimidinol with Raney nickel (M. Zimmermann, U.S. Pat. No. 3,457,278).

5-Chloro-6-cyclopropyl-4-pyrimidinol can be obtained from 6-cyclopropyl-4-pyrimidinol and N-chlorosuccimimide (M. Zimmermann, U.S. Pat. No. 3,457,278).

The 2-trifluoromethyl-4-pyrimidinols employed as starting material can be prepared by essentially the same methods used for the preparation of 2-alkyl-4-pyrimidinols as reviewed in the chapter "The Pyrimidines" (1962 and 1970) of the monograph series "The Chemistry of Heterocyclic Compounds" (Editor: A. Weissenberger, Publisher: Interscience Publisher, a Division of John Wiley and Sons).

Compounds such as, for example, 6-methyl-2-trifluoromethyl-4-pyrimidinol can also be prepared from 2,2,2-trifluoroethanimidamide and ethyl acetoacetate according to the procedure of S. Inoue, A. J. Sagginomo and E. A. Nodiff, J. Org. Chem. 26, 4504-8 (1956).

The 2-morpholino-5,6-disubstituted-4-pyrimidinols corresponding to the formula

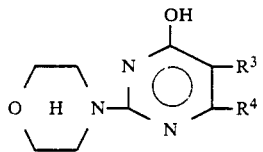

(Formula XV)

wherein $R^3$ and $R^4$ are as hereinbefore defined can be prepared prepared from the corresponding 2-methylthio-5,6-disubstituted-4-pyrimidinol according to the procedure of H. C. Van der Plas, B. Zuurdeeg and H. W. Van Meeteren, Recl. Trav. Chim. Pays-Bas 88, 1156–66 (1969).

2-Morpholino-4,6-pyrimidinediols can also be prepared from 4-morpholinecarboximidamide, sulfate and a dialkyl malonate according to the procedure of A. Cygankiewicz, R. Zimon, Z. Ryzernski and M. Gorczyca, Pal. J. Pharmacol. Pharm. 25, 391–5 (1973).

DESCRIPTION OF SOME OF THE PREFERRED EMBODIMENTS

The following examples illustrate the present invention and the manner by which it can be practiced but, as such, should not be construed as limitations upon the overall scope of the same.

EXAMPLE I:

N-Cyclopropyl O-(2-cyclopropyl-6-methyl-4-pyrimidinyl) O-ethyl phosphoramidothioate

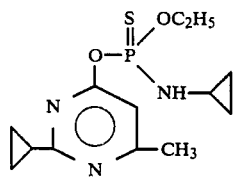

A mixture of 5.0 grams (g) of 2-cyclopropyl-6-methyl-4-pyrimidinol, 6.0 g of finely-powdered potassium carbonate, 100 ml of acetonitrile and 6.6 g of N-cyclopropyl O-ethyl phosphoramidochloridothioate was stirred, with heating to 50° C., until all of the phosphorus starting reactant had been consumed as shown by gas-liquid chromatography (GLC). The insoluble salts which formed were removed by filtration and the filtrate concentrated by evaporation under vacuum. The residue was dissolved in ether, and the ether solution was washed twice with 2 percent aqueous sodium hydroxide, once with a saturated sodium chloride solution and dried over anhydrous sodium sulfate. The solvent was removed in a rotary evaporator leaving 1.7 g (16 percent of theoretical) of the above-identified product as an amber colored oil. The product had a refractive index of n25/D = 1.5385. Upon analysis, the product was found to have carbon, hydrogen and nitrogen contents of 49.81, 6.42 and 13.03 percent, respectively, as compared with the theoretical contents of 49.81, 6.43 and 13.41 percent, respectively, as calculated for the above-named compound.

EXAMPLE II:

N-((Dimethylamino)methylene) O-ethyl O-(2-cyclopropyl-6-methyl-4-pyrimidinyl) phosphoramidothioate

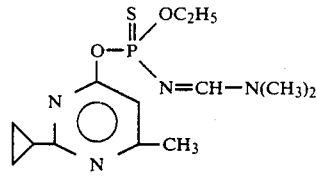

A mixture of 6.0 g of 2-cyclopropyl-6-methyl-4-pyrimidinol, 6.0 g of finely powdered potassium carbonate, 50 milliliters (ml) of acetonitrile and 7.15 g of O-ethyl phosphorodichloridothioate was stirred and heated to 60° C. until no more of the starting phosphorus compound could be detected by gas-liquid chromatography (glc). The salts which formed were removed by filtration and the filtrate cooled to 0° C. Excess ammonia was bubbled into the solution and the mixture was stirred for 16 hours and then concentrated to about 40 ml under vacuum. To this solution was added 5.88 g of dimethylformamide dimethylacetal and the mixture stirred at room temperature for one hour. The reaction mixture was concentrated under vacuum and the residue was taken up in ether. The ether solution was washed with water, a saturated sodium chloride solution and dried over anhydrous sodium sulfate. The solvent was removed in a rotary evaporator leaving 1.1 g of the above-indicated product as an amber colored oil. The product had a refractive index of n25/d = 1.5245. The infrared (IR) and nuclear magnetic resonance (NMR) spectra were consistent with the desired structure. Upon analysis, the product was found to have carbon, hydrogen and nitrogen contents of 47.16, 6.65 and 16.84 percent, respectively, as compared with the theoretical contents of 47.54, 6.45 and 17.06 percent, respectively, as calculated for the above-named structure.

EXAMPLE III:

O,O'-(2-cyclopropyl-4,6-pyrimidinediyl)O,O'-diethyl (1-methylethyl) phosphoramidothioate

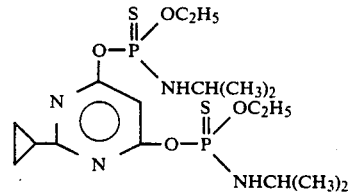

A mixture of 5.0 g of 2-cyclopropyl-4,6-pyrimidinediol 9.08 g of finely-powdered potassium carbonate, 50 ml of acetonitrile and 13.25 g of O-ethyl N-(1-methylethyl) phosphoramidochloridothioate was stirred with heating to 50° C., until all of the phosphorus starting reactant had been consumed as shown by gas-liquid chromatography (GLC). The insoluble salts were removed by filtration and the filtrate concentrated by evaporation under vacuum. The residue was dissolved in ether, and the ether solution was washed twice with 2 percent aqueous sodium hydroxide, once with saturated sodium chloride solution and dried over anhydrous sodium sulfate. The solvent was removed in a rotary evaporator leaving 2.38 g of a yellow oil. This oil was purified by high pressure liquid chromatography (HPLC) to give 0.6 g (3.8 percent of theoretical) of the above-identified product as an amber colored oil. The product had a refractive index of n25/D=1.5312. Upon analysis, the product was found to have carbon, hydrogen and nitrogen contents of 42.33, 6.80 and 11.44, respectively, as compared with the theoretical contents of 42.32, 6.68 and 11.61 percent, respectively, as calculated for the above-named compound.

EXAMPLE IV:

N-Ethyl O-(2-cyclopropyl-6-methyl-4-pyrimidinyl) O-ethyl phosphoramidothioate

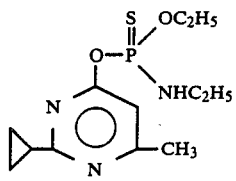

A mixture of 211 g of 2-cyclopropyl-6-methyl-4-pyrimidinol, 211 g of finely-powdered potassium carbonate, 1000 ml of acetonitrile and 263.6 g of N-ethyl O-ethyl phosphoramidochloridothioate was stirred with heating to 50° C. until all of the phosphorus starting reactant had been consumed as shown by gas-liquid chromatography (GLC). The insoluble salts were removed by filtration and the filtrate concentrated by evaporation under vacuum. The residue was dissolved in ether, and the ether solution was washed twice with 2 percent aqueous sodium hydroxide, once with saturated sodium chloride solution and dried over anhydrous sodium sulfate. The solvent was removed in a rotary evaporator leaving 372.3 g (88 percent of theoretical) of the above-identified product as an amber colored oil. The product had a refractive index of n25/D=1.5350. Upon analysis, the product was found to have carbon, hydrogen and nitrogen contents of 47.44, 6.77 and 13.84, respectively, as compared with the theoretical contents of 47.82, 6.69 and 13.94 percent, respectively, as calculated for the above-named compound.

The insecticidal compositions of the present invention are especially effective in killing and controlling insects, particularly Lepidoptera, and especially Heliothis species, which infest crops such as corn, soybeans, tobacco and particularly cotton.

Representative insects of the order Lepidoptera which can be controlled by the practice of the present invention include, for example, but are not limited to, members of the order of Lepidoptera such as the beet armyworm (*Spodoptera exigua*), the Egyptian cotton leafworm (*Spodoptera littoralis*), the black cutworm (*Agrotis ipsilon*), the pink bollworm (*Pectinophora gossypiella*), the codling moth (*Laspeyresia pomonella*) and especially members of the genus Heliothis including the tobacco budworm (*Heliothis virescens*), the corn earworm (*Heliothis zea*) and the American bollworm (*Heliothis armigera*).

Other insects controlled by the practice of the present invention, include, but are not limited to, members of the order Acarina, such as the two-spotted spider mite (*Tetranychus urticae*); members of the order Hemiptera, such as the lygus bug (*Lygus hesperus*); members of the order Coleoptera, such as the cotton boll weevil (*Anthonomus grandis*), the alfalfa weevil (*Hypera postica*), and the Western spotted cucumber beetle (*Diabrotica undecipunctata undecipunctata*); members of the order Diptera, such as the housefly (*Musca domestica*); members of the order Orthoptera, such as the German cockroach (*Blattella germanica*); members of the order Homoptera, such as the aster leafhopper (*Macrosteles fascifrons*) and the cotton aphid *(Aphis gossyppii)*.

The mixture of active compounds, i.e., active mixture of the present invention have been found to possess good activity against Heliothis species. Accordingly, the present invention also comprises methods for controlling such insects by applying to said insects and/or their habitats a pesticidally effective amount of the active mixture of compounds. For such uses the unmodified active materials of the present invention can be employed. However, the present invention embraces the use of an insecticidally-effective amount of the active materials in admixture with an inert material, as an adjuvant or carrier therefor, in solid or liquid form. Thus, for example, the active mixture can be dispersed on a finely-divided solid and employed therein as a dust. Also, the active mixture, as liquid concentrates or solid compositions comprising the active mixture, can be dispersed in water, typically with the aid of a wetting agent, and the resulting aqueous dispersion employed as a spray. In other procedures, the active mixture can be employed as a constituent of organic liquid compositions, oil-in-water and water-in-oil emulsions, or water dispersions, with or without the addition of wetting, dispersing or emulsifying agents.

Suitable adjuvants of the foregoing type are well known to those skilled in the art. The methods of applying the solid or liquid pesticidal formulations similarly are well known to the skilled artisan.

As liquid carriers or adjuvants, organic solvents there can be employed hydrocarbons, e.g., toluene, xylene, kerosene, diesel fuel, fuel oil, and petroleum naphtha, ketones such as acetone, methyl ethyl ketone and cyclohexanone, chlorinated hydrocarbons such as chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl carbitol acetate and glycerine. Mixtures of water and organic solvents, either as solutions or emulsions, can be employed.

The active mixtures can also be applied as aerosols, e.g., by dispersing them in air by means of a compressed gas such as dichlorodifluoromethane or trichlorofluoromethane and other such materials.

The active mixture of the present invention can also be applied with solid adjuvants or carriers such as talc, pyrophyllite, synthetic fine silica, attapulgus clay, kieselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl groups, alkylphenol ethylene oxide condensation products, e.g., p-isooctylphenol condensed with 10 ethylene oxide units, soaps, e.g., sodium stearate and potassium oleate, sodium salt of propylnaphthalene sulfonic acid, di-(2-ethylhexyl)-ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, Turkey Red Oil, sodium dibutyl napthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris(polyoxyethylen)-sorbitan monostearate (Tween 60), and sodium dihexyl sulfosuccinate.

The active mixture of the present invention can be applied in a formulation which contains about an equal volumetric amount, based on the volume of the active mixture present in said formulation, of (a) a polypropylene glycol having an average molecular weight from about 1,000 to about 5,000; (b) a water insoluble polybutylene glycol; and (c) mixtures and copolymers of (a) and (b). The polypropylene glycols, polybutylene glycols, their mixtures and co-polymers are all known.

The concentration of the active mixtures in liquid formulations generally is from about 0.01 to about 95 percent by weight or more. Concentrations of from about 0.1 to about 50 weight percent are often employed. In formulations to be employed as concentrates, the active materials can be present in a concentration of from about 5 to about 98 weight percent. In dusts or dry formulations, the concentration of the active ingredient can be from about 0.01 to about 95 weight percent or more; concentrations of from about 0.1 to about 50 weight percent are often conveniently employed. The active compositions can also contain other compatible additaments, for example, plant growth regulants such as herbicides or growth stimulants, pesticides such as insecticides or fungicides and the like.

The present compositions can be applied by the use of power-dusters, boom and hand sprayers, spray-dusters and by other conventional means. The compositions can also be applied from aircraft as a dust or a spray.

The active mixtures of this invention are usually applied at a rate in the range of from about 1/16 pound to about 5 pounds or more per acre, but lower or higher rates may be appropriate in some cases. A preferred application rate is from ¼ pound to about 2 pounds per acre.

EXAMPLE V

A study was conducted to determine the base-line amount in parts of the compound per million parts of the ultimate composition (ppm) of each of the hereinafter set-forth pyrimidinyl phosphorus compounds necessary to give at least 95 percent ($LD_{95}$) kill and control of Heliothis larvae.

Test solutions were prepared by admixing predetermined amounts of each of the above compounds in predetermined amounts of water containing predetermined amounts of acetone and Triton X155 surfactant.

The leaves of 5-6 week old cotton seedlings were dipped into one of the above mixtures and allowed to dry. When dry they were removed from the plant and placed into Petri dishes. Five late second instar (approximately 5 day old) tobacco budworm larvae (*Heliothis virescens*) were placed in each dish and the dishes covered. All treatments were run in triplicate. Mortality was recorded 48 hours after treatment with moribund larvae unable to crawl their own body length being counted as dead. In this test method, intoxication occurred through contact with and feeding upon treated plants.

The results of this study are set forth below in Table I.

TABLE I

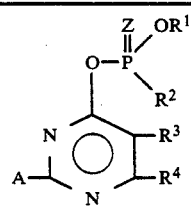

| Compound Number | A | $R^3$ | $R^4$ | $R^1$ | $R^2$ | Z | $LD_{95}$ in ppm |
|---|---|---|---|---|---|---|---|
| 1 | CP | H | H | —Et | —NHi—P | S | >200 |
| 2 | CP | H | —Me | —Me | —NHMe | S | >200 |
| 3 | CP | H | —Me | —Me | —NH—sec-B | S | >200 |
| 4 | CP | H | —Me | —Et | —NHMe | S | >200 |
| 5 | CP | H | —Me | —Et | —NHEt | S | >200 |
| 6 | CP | H | —Me | —Et | —NH—i-P | S | >200 |
| 7 | CP | H | —Me | —Et | —NH—n-P | S | >200 |
| 8 | CP | H | —Me | —Et | —NHCP | S | >200 |
| 9 | CP | H | —Me | —Et | —NH—sec-B | S | >200 |
| 10 | CP | H | —Me | —Et | —NHA | S | >200 |
| 11 | CP | H | —Me | —Et | —N(Me)$_2$ | S | >200 |
| 12 | CP | H | —Me | —Et | —N—Dman | S | >200 |
| 13 | CP | H | —n-P | —Et | —NH—i-P | S | >200 |
| 14 | CP | H | —MeSEt | —Et | —NH—i-P | S | >200 |
| 15 | CP | H | —CF$_3$ | —Et | —NH—i-P | S | >200 |

TABLE I-continued

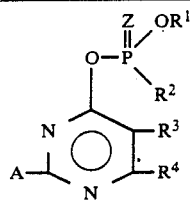

| Compound Number | A | R³ | R⁴ | R¹ | R² | Z | LD₉₅ in ppm |
|---|---|---|---|---|---|---|---|
| 16 | CP | H | —Cl | —Et | —NHEt | N | >200 |
| 17 | CP | H | —Cl | —Et | —NH—i-P | S | >200 |
| 18 | CP | H | —SEt | —Et | —NH—i-P | S | >200 |
| 19 | CP | —Me | —Me | —Et | —NH—i-P | S | >200 |
| 20 | CP | —Cl | —Me | —Et | —NHEt | S | >200 |
| 21 | CP | —H | @* | —Et | —NH—i-P | S | >200 |
| 22 | 1-Me—CP | H | —Me | —Et | —NH—i-P | S | >200 |
| 23 | 1-Me—CP | H | —CF₃ | —Et | —NH—i-P | S | >200 |
| 24 | CB | H | —Me | —Et | —NH—i-P | S | >200 |
| 25 | Ph | H | —Me | —Et | —NH—i-P | S | >200 |
| 26 | H | H | —Cp | —Et | —NH—Et | S | >200 |
| 27 | Me | H | —Me | —Et | —NHEt | S | >200 |
| 28 | Me | H | —CP | —Et | —NHEt | O | >200 |
| 29 | Me | H | —CP | —Et | —NH—i-P | S | >200 |
| 30 | i-P | H | —Me | —Et | —NH—i-P | S | >200 |
| 31 | t-B | H | —Me | —Et | —NHEt | S | >200 |
| 32 | t-B | H | —Me | —Et | —NH—i-P | S | >200 |
| 33 | t-B | H | —MeOMe | —Et | —NH—i-P | S | >200 |
| 34 | t-B | H | —MeSEt | —Et | —NH—i-P | S | >200 |
| 35 | t-B | H | —Cl | —Et | —NHEt | S | >200 |
| 36 | t-B | H | —Cl | —Et | —NH—i-P | S | >200 |
| 37 | t-B | H | —SEt | —Et | —NH—i-P | S | >200 |
| 38 | PH | H | —Me | —Et | —NHEt | S | >200 |
| 39 | CF₃ | H | —Me | —Et | —NH—i-P | S | >200 |
| 40 | SEt | H | —Me | —Et | —NH—i-P | S | >200 |
| 41 | S—i-P | H | —CP | —Et | —NH—Et | S | >200 |
| 42 | S—Al | H | —Me | —Et | —NH—i-P | S | >200 |
| 43 | N(Me)₂ | H | —Me | —Et | —NH—i-P | S | >200 |
| 44 | N(Me)₂ | H | —CP | —Et | —NH—Et | S | >200 |
| 45 | Mor | H | —Me | —Et | —NH—i-P | S | >200 |
| 46 | i-P | H | —Me | —Et | —NH—Et | S | >200 |

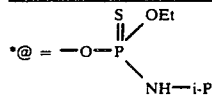

CP = cyclopropyl
1-Me—CP = 1-methylcyclopropyl
CP—Me = cyclopropylmethyl
CB = cyclobutyl
Me = methyl
Et = ethyl
i-P = isopropyl
sec-B = secondary butyl
t-B = tertiary butyl
Ph = phenyl
Mor = morpholino
OEt = ethoxy
SEt = ethylthio
NHMe = methylamino
NHEt = ethylamino
NH—i-P = isopropylamino
NH—n-P = n-propylamino
NH—t-B = tert. butylamino
NH—i-B = isobutylamino
MeOMe = methoxymethyl
NH—sec-B = secondary butylamino
NH—n-B = n-butylamino
NH—CP = cyclopropylamino
N(Me)₂ = dimethylamino
N(i-P)₂ = diisopropylamino
NHAl = Allylamino
N—Dman = ((dimethylamino)-methylene)amino
—MeSEt = Ethylthiomethyl
S—Al = allylthio

EXAMPLE VI

A study was conducted to determine the effectiveness and enhancing response of various combinations of O,O-diethyl O-(3,5,6-trichloro-2-pyridnyl) phosphorothioate and O-(2-cyclopropyl-6-methyl-4-pyrimidinyl) O-ethyl N-(1-methylethyl)phosphoramidothioate (Compound 6) in the control of Heliothis larvae.

Test solutions were prepared by admixing predetermined amounts of each of the above compounds in predetermined amounts of water containing predetermined amounts of acetone and Triton X155 surfactant.

The leaves of 5-6 week old cotton seedlings were dipped into one of the above mixtures and allowed to dry. When dry they were removed from the plant and placed into Petri dishes. Five late second instar (approximately 5 day old) tobacco budworm larvae (*Heliothis virescens*) were placed in each dish and the dishes covered. All treatments were run in triplicate. Mortality was recorded 48 hours after treatment with moribund larvae unable to crawl their own body length being counted as dead. In this test method, intoxication occurred through contact with and feeding upon treated plants.

The results of this study are set forth below in Table II.

phorothioate and O-(2-cyclopropyl-6-methyl-4-pyrimidinyl) O-ethyl N-(1-methylethyl)phosphoramidothioate in the control of Heliothis larvae.

Test solutions were prepared by admixing predetermined amounts of each of the above compounds in predetermined amounts of water containing predetermined amounts of acetone and Triton X155 surfactant.

The leaves of 5-6 week old cotton seedlings were dipped into one of the above mixtures and allowed to dry. When dry they were removed from the plant and placed into Petri dishes. Five late second instar (approximately 5 day old) tobacco budworm larvae (*Heliothis virescens*) were placed in each dish and the dishes covered. All treatments were run in triplicate. Mortality was recorded 48 hours after treatment with moribund larvae unable to crawl their own body length being

TABLE II

| Test No.[1] | Chemical[2] | Amount in PPM | Chemical[3] | Amount in PPM | Ratio of A to B | Expected Control in Percent[4] | Actual Control in Percent | Percent Increase Over Expected Control[5] |
|---|---|---|---|---|---|---|---|---|
| 1 | — | — | — | — | — | — | 0 | — |
| 2 | A | 12.5 | — | — | — | — | 7 | — |
| 3 | A | 25 | — | — | — | — | 7 | — |
| 4 | A | 50 | — | — | — | — | 7 | — |
| 5 | A | 100 | — | — | — | — | 67 | — |
| 6 | — | — | B | 12.5 | — | — | 0 | — |
| 7 | — | — | B | 25 | — | — | 7 | — |
| 8 | — | — | B | 50 | — | — | 13 | — |
| 9 | — | — | B | 100 | — | — | 33 | — |
| 10 | A | 12.5 | B | 12.5 | 1:1 | 7 | 60 | 757 |
| 11 | A | 12.5 | B | 25 | 1:2 | 14 | 87 | 521 |
| 12 | A | 12.5 | B | 50 | 1:4 | 19 | 93 | 389 |
| 13 | A | 12.5 | B | 100 | 1:8 | 38 | 100 | 163 |
| 14 | A | 25 | B | 12.5 | 2:1 | 7 | 60 | 757 |
| 15 | A | 25 | B | 25 | 1:1 | 14 | 100 | 614 |
| 16 | A | 25 | B | 50 | 1:2 | 19 | 100 | 426 |
| 17 | A | 25 | B | 100 | 1:4 | 38 | 100 | 163 |
| 18 | A | 50 | B | 12.5 | 4:1 | 7 | 73 | 904 |
| 19 | A | 50 | B | 25 | 2:1 | 14 | 93 | 564 |
| 20 | A | 50 | B | 50 | 1:1 | 19 | 93 | 389 |
| 21 | A | 50 | B | 100 | 1:2 | 38 | 100 | 163 |
| 22 | A | 100 | B | 12.5 | 8:1 | 67 | 87 | 29 |
| 23 | A | 100 | B | 25 | 4:1 | 69 | 100 | 44 |
| 24 | A | 100 | B | 50 | 2:1 | 79 | 100 | 26 |
| 25 | A | 100 | B | 100 | 1:1 | 78 | 100 | 28 |

[1]Test Nos. 1-9 are control runs with Test 1 being a no chemical control (surfactant/acetone/water alone).
[2]Chemical A represents O,O—diethyl O—(3,5,6-trichloro-2-pyridinyl) phosphorothioate.
[3]Chemical B represents O—(2-cyclopropyl-6-methyl-4-pyrimidinyl)O—ethyl N—(1-methylethyl)-phosphoramidothioate.
[4]Expected control equals % control by chemical A + % control by chemical B (minus) (−)

$$\frac{\% \text{ control by chemical A} \times \% \text{ control chemical B}}{100}$$

[5]Percent increase over expected control equals $\frac{\text{actual control}}{\text{expected control}} \times 100 - 100$

EXAMPLE VII

A study was conducted to determine the effectiveness and enhancing response of various combinations of O,O-dimethyl O-(3,5,6-trichloro-2-pyridinyl) phoscounted as dead. In this test method, intoxication occurred through contact with and feeding upon treated plants.

The results of this study are set forth below in Table III.

TABLE III

| Test No.[1] | Chemical[2] | Amount in PPM | Chemical[3] | Amount in PPM | Ratio of A to B | Expected Control in Percent[4] | Actual Control in Percent | Percent Increase Over Expected Control[5] |
|---|---|---|---|---|---|---|---|---|
| 1 | — | — | — | — | — | — | 0 | — |
| 2 | A | 6.25 | — | — | — | — | 0 | — |
| 3 | A | 12.5 | — | — | — | — | 27 | — |
| 4 | A | 25 | — | — | — | — | 27 | — |
| 5 | A | 50 | — | — | — | — | 20 | — |
| 6 | A | 100 | — | — | — | — | 40 | — |
| 7 | — | — | B | 6.5 | — | — | 0 | — |
| 8 | — | — | B | 12.5 | — | — | 0 | — |
| 9 | — | — | B | 25 | — | — | 13 | — |
| 10 | — | — | B | 50 | — | — | 18 | — |
| 11 | — | — | B | 100 | — | — | 12 | — |
| 12 | A | 6.5 | B | 6.5 | 1:1 | 0 | 0 | 0 |

TABLE III-continued

| Test No.[1] | Chemical[2] | Amount in PPM | Chemical[3] | Amount in PPM | Ratio of A to B | Expected Control in Percent[4] | Actual Control in Percent | Percent Increase Over Expected Control[5] |
|---|---|---|---|---|---|---|---|---|
| 13 | A | 12.5 | B | 12.5 | 1:1 | 27 | 13 | −52 |
| 14 | A | 25 | B | 25 | 1:1 | 36 | 60 | 67 |
| 15 | A | 50 | B | 50 | 1:1 | 35 | 100 | 186 |
| 16 | A | 100 | B | 100 | 1:1 | 47 | 100 | 113 |

[1]Test Nos. 1-11 are control runs with Test 1 being a no chemical control (surfactant/acetone/water alone).
[2]Chemical A represents O,O—dimethyl O—(3,5,6-trichloro-2-pyridinyl) phosphorothioate.
[3]Chemical B represents O—(2-cyclopropyl-6-methyl-5-pyrimidinyl) O—ethyl N—(1-methylethyl) phosphoramidothioate.
[4]Expected control equals % control by chemical A + % control by chemical B (minus) (−)

$$\frac{\% \text{ control by chemical A} \times \% \text{ control chemical B}}{100}$$

[5]Percent increase over expected control equals $\frac{\text{actual control}}{\text{expected control}} \times 100 - 100$

EXAMPLE VIII

A study was conducted to determine the amount in parts of active compound per million parts of the ultimate compositions (ppm) of O,O-diethyl O-(3,5,6-trichloro-2-pyridinyl) phosphorothioate, alone, and in a 1:1 ratio of said compound with one of the compounds set forth in Example V necessary to give at least a 95 percent ($LD_{95}$) kill and control of Heliothis larvae.

Test solutions were prepared by admixing predetermined amounts of each of the above compounds in predetermined amounts of water containing predetermined amounts of acetone and Triton X155 surfactant. The leaves of 5-6 week old cotton seedlings were dipped into one of the above mixtures and allowed to dry. When dry they were removed from the plant and placed into Petri dishes. Five late second instar (approximately 5 day old) tobacco budworm larvae (*Heliothis virescens*) were placed in each dish and the dishes covered. All treatments were run in triplicate. Mortality was recorded 48 hours after treatment with moribund larvae unable to crawl their own body length being counted as dead. In this test method, intoxication occurred through contact with and feeding upon treated plants.

The results of this study are set forth below in Table IV.

TABLE IV (O,O—Diethyl O—(3,5,6-Trichloro-2-pyridinyl) phosphorothioate, alone)

$$\frac{LD_{95}}{600 \text{ ppm}}$$

$LD_{95}$ of 1:1 Ratio of O,O—diethyl O—(3,5,6-trichloro-2-pyridinyl) phosphorothioate with indicated compound from Example IV. Amount listed under $LD_{95}$ is amount of each compound in PPM present. $LD_{95}$ for each compound from Example IV alone is > 200 ppm.

| Compound | $LD_{95}$ | Compound | $LD_{95}$ | Compound | $L_{95}$ |
|---|---|---|---|---|---|
| 1 | 40 | 16 | 27 | 31 | 35 |
| 2 | 50 | 17 | 28 | 32 | 75 |
| 3 | 150 | 18 | 20–50 | 33 | 50 |
| 4 | 30 | 19 | 75 | 34 | 50 |
| 5 | 26 | 20 | 30 | 35 | 30 |
| 6 | 33 | 21 | 80 | 36 | 30 |
| 7 | 35 | 22 | 125 | 37 | 100 |
| 8 | 28 | 23 | 75 | 38 | 40 |
| 9 | 80 | 24 | 40 | 39 | 70 |
| 10 | 50 | 25 | 80 | 40 | 30 |
| 11 | 120 | 26 | 35 | 41 | 80 |
| 12 | 50 | 27 | 25 | 42 | 70 |
| 13 | 50 | 28 | 40 | 43 | 60 |
| 14 | 65 | 29 | 40 | 44 | 45 |
| 15 | 75 | 30 | 80 | 45 | 100 |

TABLE IV-continued (O,O—Diethyl O—(3,5,6-Trichloro-2-pyridinyl) phosphorothioate, alone)

$$\frac{LD_{95}}{600 \text{ ppm}}$$

$LD_{95}$ of 1:1 Ratio of O,O—diethyl O—(3,5,6-trichloro-2-pyridinyl) phosphorothioate with indicated compound from Example IV. Amount listed under $LD_{95}$ is amount of each compound in PPM present. $LD_{95}$ for each compound from Example IV alone is > 200 ppm.

| Compound | $LD_{95}$ | Compound | $LD_{95}$ | Compound | $L_{95}$ |
|---|---|---|---|---|---|
|  |  |  |  | 46 | 25 |

What is claimed is:

1. An insecticidal composition which comprises an inert carrier and an insecticidally effective amount of an active mixture of toxicants which mixture comprises about 1 part by weight of a pyridinyl phosphorus insecticide corresponding to the formula

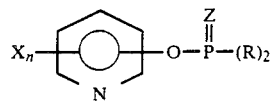

wherein each X independently represents bromo, chloro, fluoro or iodo; Z represents oxygen or sulfur; each R independently represents alkoxy of 1 to 4 carbon atoms and n represents an integer of from 1 to 3 in admixture with from about 1/16 part to about 16 parts by weight of a pyrimidinyl compound corresponding to the formula

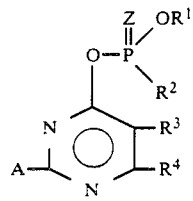

wherein A represents hydrogen, alkyl of 1 to 4 carbon atoms, alkylthio of 1 to 4 carbon atoms, allylthio, cycloalkyl of 3 or 4 carbon atoms, alkyl(cycloalkyl) wherein the alkyl group is of 1 to 4 carbon atoms and the cycloalkyl group is of 3 or 4 carbon atoms, (cycloalkyl)alkyl wherein the alkyl group is of 1 to 4 carbon atoms and the cycloalkyl group is of 3 or 4 carbon atoms, phenyl, trifluoromethyl, dialkylamino wherein each alkyl group is independently of 1 to 4 carbon atoms or morpholino; $R^4$ represents hydrogen, chloro, trifluoromethyl, alkyl of 1 to 4 carbon atoms or alkylthio of 1 to 4 carbon atoms (alkylthio)alkyl wherein each alkyl group is independently of 1 to 4 carbon atoms, alkoxyalkyl wherein the alkoxy and alkyl groups are independently of 1 to 4 carbon atoms, cycloalkyl of 3 or 4 carbon atoms or a group of the formula

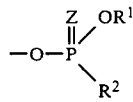

$R^1$ represents alkyl of 1 to 4 carbon atoms; $R^2$ represents monoalkylamino of 1 to 4 carbon atoms, dialkylamino wherein each alkyl group is independently of 1 to 4 carbon atoms, allylamino, ((dimethylamino)methylene)amino (—N=CH—N(CH$_3$)$_2$ or monocycloalkylamino of 3 to 4 carbon atoms; $R^3$ represents hydrogen, chloro, bromo, fluoro or methyl and Z is oxygen or sulfur.

2. The composition as defined in claim 1 wherein the inert carrier is an inert liquid carrier.

3. The composition as defined in claim 2 wherein the active mixture of toxicants is present in an amount of from about 0.01 to about 95 percent by weight of the total composition.

4. The composition as defined in claim 3 wherein the composition is present as an aqueous dispersion and the mixture of toxicants is present in an amount of from about 0.1 to about 50 percent by weight of the total composition.

5. The composition as defined in claim 1 wherein the pyridinyl phosphorus insecticide is O,O-diethyl O-(3,5,6-trichloro-2-pyridinyl) phosphorothioate.

6. The composition as defined in claim 1 wherein the pyridinyl phosphorus insecticide is O,O-dimethyl O-(3,5,6-trichloro-2-pyridinyl) phosphorothioate.

7. The composition as defined in claim 5 wherein the pyrimidinyl compound is O-(6-chloro-2-cyclopropyl-4-pyrimidinyl) O-ethyl N-(1-methylethyl) phosphoramidothioate.

8. The composition as defined in claim 5 wherein the pyrimidinyl compound is O-(5-chloro-2-cyclopropyl-6-methyl-4-pyrimidinyl) O-ethyl N-ethyl phosphoramidothioate.

9. The composition as defined in claim 5 wherein the pyrimidinyl compound is N-cyclopropyl O-(2-cyclopropyl-6-methyl-4-pyrimidinyl) O-ethyl phosphoramidothioate.

10. The composition as defined in claim 5 wherein the pyrimidinyl compound is N-ethyl O-ethyl O-(6-methyl-2-(1-methylethyl)-4-pyrimidinyl) phosphoramidothioate.

11. The composition as defined in claim 5 wherein the pyrimidinyl compound is O-(6-chloro-2-cyclopropyl-4-pyrimidinyl) O-ethyl N-ethyl phosphoramidothioate.

12. The composition as defined in claim 5 wherein the pyrimidinyl compound is O-(2,6-dimethyl-4-pyrimidinyl) O-ethyl N-ethyl phosphoramidothioate.

13. The composition as defined in claim 5 wherein the pyrimidinyl compound is O-(6-chloro-2-(1,1-dimethylethyl)-4-pyrimidinyl) O-ethyl N-ethyl phosphoramidothioate.

14. The composition as defined in claim 5 wherein the pyrimidinyl compound is O-(6-chloro-2-(1,1-dimethylethyl)-4-pyrimidinyl) O-ethyl N-(1-methylethyl) phosphoramidothioate.

15. The composition as defined in claim 9. wherein the pyrimidinyl compound is O-ethyl O-(2-ethylthio-6-methyl-4-pyrimidinyl) N-(1-methylethyl) phosphoramidothioate.

16. The composition as defined in claim 5 wherein the pyrimidinyl compound is O-(2-cyclopropyl-6-methyl-4-pyrimidinyl) O-ethyl N-methyl phosphoramidothioate.

17. A composition as defined in claim 5 wherein the pyrimidinyl compound is O-(2-cyclopropyl-6-methyl-4-pyrimidinyl) N-ethyl O-ethyl phosphoramidothioate.

18. A method for killing and controlling insects of the genus Heliothis which comprises contacting said insects or their habitat with an insecticidally effective amount of a composition which comprises an inert carrier in intimate admixture with an active mixture of toxicants which mixture comprises about 1 part by weight of a pyridinyl phosphorus insecticide corresponding to the formula

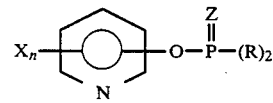

wherein each X independently represents bromo, chloro, fluoro or iodo; Z represents oxygen or sulfur; each R independently represents alkoxy of 1 to 4 carbon atoms and n represents an integer of from 1 to 3 in admixture with from about 1/16 part to about 16 parts by weight of a pyrimidinyl compound corresponding to the formula

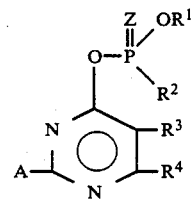

wherein A represents hydrogen, alkyl of 1 to 4 carbon atoms, alkylthio of 1 to 4 carbon atoms, allylthio, cycloalkyl of 3 or 4 carbon atoms, alkyl(cycloalkyl) wherein the alkyl group is of 1 to 4 carbon atoms and the cycloalkyl group is of 3 or 4 carbon atoms, (cycloalkyl)alkyl wherein the alkyl group is of 1 to 4 carbon atoms and the cycloalkyl group is of 3 or 4 carbon atoms, phenyl, trifluoromethyl, dialkylamino wherein each alkyl group is independently of 1 to 4 carbon atoms or morpholino; $R^1$ represents alkyl of 1 to 4 carbon atoms; $R^2$ represents monoalkylamino of 1 to 4 carbon atoms, dialkylamino wherein each alkyl group is independently of 1 to 4 carbon atoms, allylamino, ((dimethylamino)methylene)amino (—N=CH—N=CH$_3$=$_2$ or monocycloalkylamino of 3 to 4 carbon atoms; $R^3$ represents hydrogen, chloro, bromo, fluoro or methyl; $R^4$ represents hydrogen, chloro, trifluoromethyl, alkyl of 1 to 4 carbon atoms or alkylthio of 1 to 4 carbon atoms (alkylthio)alkyl wherein each alkyl group is independently of 1 to 4 carbon atoms, alkoxyalkyl wherein the alkoxy and alkyl groups are independently of 1 to 4 carbon atoms, cycloalkyl of 3 or 4 carbon atoms or a group of the formula

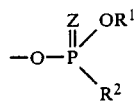

and Z is oxygen or sulfur.

19. The method as defined in claim 18 wherein the composition is employed in amounts of from about 1/16 pound to about 5 pounds per acre.

20. The method as defined in claim 18 wherein the active pyridinyl phosphorus insecticide is O,O-diethyl O-(3,5,6-trichloro-2-pyridinyl) phosphorothioate.

21. The method as defined in claim 18 wherein the active pyridinyl phosphorus insecticide is O,O-dimethyl O-(3,5,6-trichloro-2-pyridinyl) phosphorothioate.

22. The method as defined in claim 18 wherein the active pyrimidinyl compound is O-(6-chloro-2-cyclopropyl-4-pyrimidinyl) O-ethyl N-(1-methylethyl) phosphoramidothioate.

23. The method as defined in claim 18 wherein the active pyrimidinyl compound is O-(5-chloro-2-cyclopropyl-6-methyl-4-pyrimidinyl) O-ethyl N-ethyl phosphoramidothioate.

24. The method as defined in claim 18 wherein the active pyrimidinyl compound is N-cyclopropyl O-(2-cyclopropyl-6-methyl-4-pyrimidinyl) O-ethyl phosphoramidothioate.

25. The method as defined in claim 18 wherein the active pyrimidinyl compound is N-ethyl O-ethyl O-(6-methyl-2-(1-methylethyl)-4-pyrimidinyl) phosphoramidothioate.

26. The method as defined in claim 18 wherein the active pyrimidinyl compound is O-(6-chloro-2-cyclopropyl-4-pyrimidinyl) O-ethyl N-ethyl phosphoramidothioate.

27. The method as defined in claim 18 wherein the active pyrimidinyl compound is O-(2,6-dimethyl-4-pyrimidinyl) O-ethyl N-ethyl phosphoramidothioate.

28. The method as defined in claim 18 wherein the active pyrimidinyl compound is O-(6-chloro-2-(1,1-dimethylethyl)-4-pyrimidinyl) O-ethyl N-ethyl phosphoramidothioate.

29. The method as defined in claim 18 wherein the active pyrimidinyl compound is O-(6-chloro-2-(1,1-dimethylethyl)-4-pyrimidinyl O-ethyl N-(1-methylethyl) phosphoramidothioate.

30. The method as defined in claim 18 wherein the active pyrimidinyl compound is 0-ethyl O-(2-ethylthio-6-methyl-4-pyrimidinyl) N-(1-methylethyl) phosphoramidothioate.

31. The method as defined in claim 18 wherein the active pyrimidinyl compound is O-(2-cyclopropyl-6-methyl-4-pyrimidinyl) O-ethyl N-methyl phosphoramidothioate.

32. The method as defined in claim 18 wherein the active pyrimidinyl compound is O-(2-cyclopropyl-6-methyl-4-pyrimidinyl) N-ethyl O-ethyl phosphoramidothioate.

* * * * *

UNITED STATES PATENT AND TRADEMARK OFFICE
CERTIFICATE OF CORRECTION

PATENT NO. : 4,489,068

DATED : December 18, 1984

INVENTOR(S) : Donald H. DeVries, Walter Reifschneider and Mark J. Costales

It is certified that error appears in the above-identified patent and that said Letters Patent is hereby corrected as shown below:

Col. 7, line 3, "N-cyclopropy" should read -- N-cyclopropyl --.

Col. 13, line 26, that portion of the sentence reading "(polyoxyethylen)" should read -- (polyoxyethylene) --.

Col. 15, line 67, "pyridnyl" should read -- pyridinyl --.

Col. 17, Table II, footnote 4, delete the parenthesis signs around the word "minus".

Col. 19, Table III, footnote 4, delete the parenthesis signs around the word "minus".

Col. 19, line 56, the last column heading reading "$L_{95}$" should read -- $LD_{95}$ --.

Col. 20, line 28, the last column heading reading "$L_{95}$" should read -- $LD_{95}$ --.

UNITED STATES PATENT AND TRADEMARK OFFICE
CERTIFICATE OF CORRECTION

PATENT NO. : 4,489,068

DATED : December 18, 1984

INVENTOR(S) : Donald H. DeVries, Walter Reifschneider and Mark J. Costales

Page 2 of 2

It is certified that error appears in the above-identified patent and that said Letters Patent is hereby corrected as shown below:

Col. 22, line 3, the period should be deleted after the numeral "9".

Col. 22, line 59, that portion of the formula reading "=$CH_3=_2$ should read -- $(CH_3)_2$ --.

Signed and Sealed this

Third Day of September 1985

[SEAL]

Attest:

DONALD J. QUIGG

Attesting Officer  Acting Commissioner of Patents and Trademarks - Designate